United States Patent
Hubbard et al.

[11] Patent Number: 5,454,389
[45] Date of Patent: Oct. 3, 1995

[54] OSTOMY BAG CLEANING DEVICE

[76] Inventors: John C. Hubbard; Beatrice Hubbard, both of 501 Carwynn Rd., La Follette, Tenn. 37766

[21] Appl. No.: 308,666

[22] Filed: Sep. 19, 1994

[51] Int. Cl.⁶ .................................................. B08B 3/02
[52] U.S. Cl. .................. 134/104.4; 134/113; 134/198; 134/201; 134/166 R; 134/167 R; 604/277; 604/355
[58] Field of Search ..................... 239/126, 124, 239/532; 134/56 R, 113, 198, 104.4, 166 R, 167 R, 201; 604/118, 65, 150, 151, 179, 247, 277, 187, 279, 310, 355, 356, 345, 331, 332, 334, 339; 2/300

[56] References Cited

U.S. PATENT DOCUMENTS

| | | | |
|---|---|---|---|
| 2,706,985 | 4/1955 | White | 604/355 X |
| 3,055,365 | 9/1962 | Tezak | 604/179 X |
| 3,508,546 | 4/1970 | Rogers et al. | 68/151 X |
| 3,762,411 | 10/1973 | Lloyd et al. | 604/151 |
| 3,773,046 | 11/1973 | Rosenberg | 604/151 |
| 3,783,867 | 1/1974 | Summersby et al. | 604/151 |
| 4,178,931 | 12/1979 | Lind et al. | 604/151 |
| 4,411,659 | 10/1983 | Jensen et al. | 604/332 |
| 4,642,106 | 2/1987 | Downey | 604/332 |
| 4,668,227 | 5/1987 | Kay | 604/277 X |
| 4,810,250 | 5/1987 | Ellenberg et al. | 604/277 |
| 5,037,408 | 8/1991 | Henry | 604/332 |
| 5,071,409 | 12/1991 | Rosenberg | 604/187 |
| 5,096,503 | 3/1992 | Wellman | 134/22.18 |
| 5,098,420 | 3/1992 | Iacone | 604/338 |

OTHER PUBLICATIONS

"The First Step" by Hospital Educators Resourse Catalogue Inc., 1989.

*Primary Examiner*—Frankie L. Stinson
*Attorney, Agent, or Firm*—Pitts & Brittian

[57] ABSTRACT

An ostomy bag cleaning device (10) for introducing water into an ostomy bag (12) in order to loosen and evacuate waste contained therein and retain evacuated waste material until sanitarily disposal thereof. The cleaning device (10) includes a pump reservoir (14) for storing clean water to be used as a cleaning medium for an ostomy bag (12). A pump (16) includes a pump impeller (26) positioned within the pump reservoir (14) such that the water may be withdrawn therefrom. Water is withdrawn from the pump reservoir (14) through a flexible hose (38). A waste receptacle (18) is provided for receiving and storing the waste and wasted water from the ostomy bag (12) until sanitary disposal thereof. A carrying case (42) is provided for storing the pump reservoir (14), the pump (16), the waste receptacle (18), and any associated equipment. A rigid support structure (44) is provided for receiving both the pump reservoir (14) and the waste receptacle (18) such that the position of each is maintained. A strap member (52) is provided for carrying the carrying case (42) and for supporting the cleaning device (10) while being used to clean an ostomy bag (12). The carrying case (42) is also provided with a engaging device (54) for securing a garment thereto.

20 Claims, 2 Drawing Sheets

OSTOMY BAG CLEANING DEVICE

TECHNICAL FIELD

This invention relates to the field of ostomy or colostomy bags. More specifically, this invention relates to a device for evacuating and cleaning ostomy and colostomy bags in a sanitary manner.

BACKGROUND ART

It is well known that many people are required to use body waste bags after undergoing colostomy, ileostomy, or other similar surgery on their intestinal or urinary tract. It is also well known that such body waste bags must be periodically evacuated and sanitized. For simplicity of understanding, the term "ostomy bag" is hereinafter used to indicate any type of body waste bag, including but not limited to, colostomy bags, ileostomy bags, and the like.

Typically, the process involves evacuating the ostomy bag into a toilet or sink using the pressure of the tap water or pressure created by elevating a volume of water above the ostomy bag. The water from either of these sources is introduced into the ostomy bag and is used to loosen waste from the bag and finally as a medium for carrying the waste out of the bag. One such method is described in detail in *The First Step: guidelines on care and recovery following colostomy surgery*, Kay Marshall, Hospital Educators Resource Catalogue, Inc., Lincoln, Neb., 1989, at pages 15–17. Other devices have been produced to aid in the evacuation and cleaning of ostomy bags, such as those disclosed in the following U.S. patents:

| U.S. Pat. No. | Inventor(s) | Issue Date |
| --- | --- | --- |
| 4,642,106 | W. Downey | Feb 10, 1987 |
| 5,037,408 | J. S. Henry | Aug 6, 1991 |
| 5,096,503 | S. E. Wellman | Mar 17, 1992 |

The method discussed by Marshall in *The First Step* provides for the use of an elevated water source to generate pressure for the introduction of water. The patient is seated on a commode while the water is introduced into the ostomy bag and the body waste is evacuated.

Downey ('106) discloses a device for evacuating the contents of an ostomy pouch wherein a pair of elongated members are spaced apart a small distance, the ostomy bag being inserted between the elongated members and then pulled through. As the ostomy bag is pulled between the elongated members, the contents are forced out.

The device taught by Henry ('408) is simply a tool designed to be secured to an ostomy bag proximate the stoma opening such that the ostomy bag may be manipulated within a toilet in order to facilitate the evacuate of the contents from within the ostomy bag. This particular device requires that one place his hands within the toilet with the distinct possibility of contaminating them.

Finally, in the device taught by Wellman ('503), an attachment device is provided for securing a hose to a water faucet associated with a sink. A terminal end of the hose is inserted within an ostomy bag such that the running water serves to dislodge any waste from the interior of the bag. However, this device requires that the ostomy bag be cleaned within a sink. Obviously, this creates unsanitary conditions with respect to the use of the particular sink.

A well known problem with evacuating and cleaning an ostomy bag presents itself when the patient is away from home. Using public rest rooms is often unsanitary or impossible if the required facilities are not available. It is also often undesirable to clean an ostomy bag using the facilities in another's dwelling for fear of creating an unsanitary environment.

Therefore, it is an object of the present invention to provide a device that may be used at or away from home to assist in the evacuation and sanitation of a colostomy bag.

Another object of the present invention is to provide a means whereby waste and wasted water are stored in a sanitary container for future disposal.

DISCLOSURE OF THE INVENTION

Other objects and advantages will be accomplished by the present invention which serves to introduce water into an ostomy bag in order to loosen waste contained therein and to assist in evacuating that waste. Moreover, in the preferred embodiment the cleaning device is designed to retain evacuated waste material until the waste material can be sanitarily disposed.

The cleaning device of the present invention is comprised generally of a pump reservoir, a pump, and a waste receptacle. The pump reservoir stores clean water to be used as a cleaning medium for an ostomy bag. The pump includes a pump impeller positioned within the pump reservoir such that the water may be withdrawn therefrom. The pump impeller is received within the pump reservoir through the removable lid.

The pump is defines an outlet which is placed in communication with a flexible hose. Water is withdrawn from the pump reservoir via the pump impeller and through the flexible hose. In order to equalize the pressure within the pump reservoir, a selectively opened vent is provided. The waste receptacle is provided for receiving and storing the waste and wasted water from the ostomy bag until sanitary disposal thereof.

A carrying case is provided for storing the pump reservoir, the pump, the waste receptacle, and any associated equipment. A rigid support structure is provided for receiving both the pump reservoir and the waste receptacle such that the position of each is maintained. In order to better maintain the position of the pump reservoir and waste receptacle within the support structure, a fastening member such as a hook-and-loop fastener may be used. The support structure is received within a carrying case having an opening proximate the top thereof. The carrying case defines a substantially rectangular configuration dimensioned to closely receive the support structure, the pump reservoir, the waste receptacle, and any other associated components. A strap member is provided for carrying the carrying case and for supporting the cleaning device while being used to clean an ostomy bag. The strap member allows one to stand while performing the cleaning procedure. The carrying case is also provided with a pair of hooks for securing a belt loop thereto.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

Figure 1:
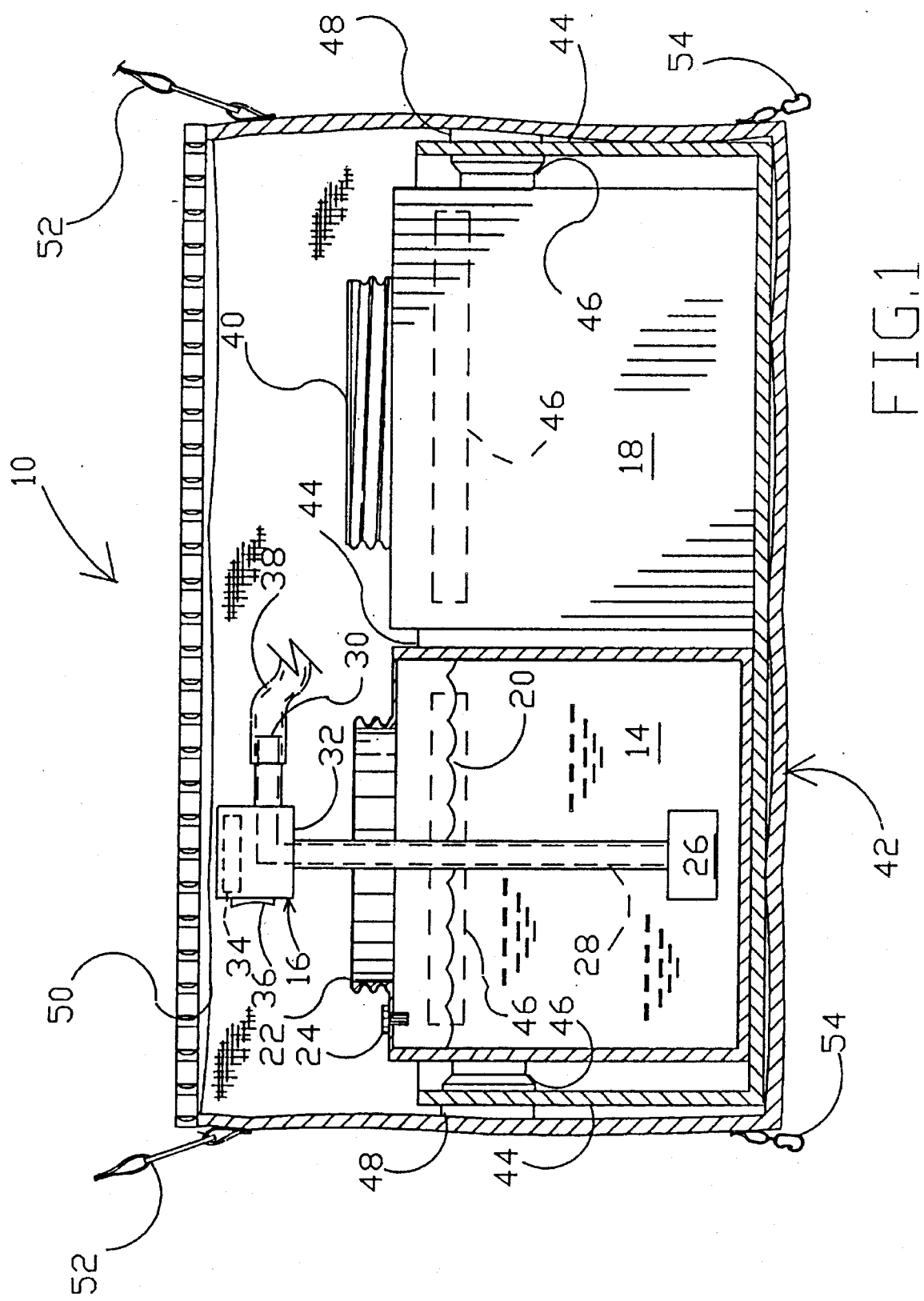
FIG. 1 is an elevational view, partially in section, of the ostomy bag cleaning device constructed in accordance with several features of the present invention.

A device for cleaning an ostomy bag incorporating various features of the present invention is illustrated generally at 10 in the figures. The cleaning device 10 is designed for introducing water 20 into an ostomy bag 12 in order to loosen waste contained therein and for assisting in evacuating that waste. Moreover, in the preferred embodiment the cleaning device 10 is designed to retain evacuated waste material until the waste material can be sanitarily disposed.

The cleaning device 10 of the present invention is comprised generally of a pump reservoir 14, a pump 16, and a waste receptacle 18. The pump reservoir 14 is used primarily to store clean water 20 to be used as a cleaning medium for an ostomy bag 12. A removable lid 22 is provided for refilling the reservoir 14 after use. The pump 16 may be any conventional type pump including a pump impeller 26. The pump impeller 26 is positioned within the pump reservoir 14 such that the water 20 may be withdrawn therefrom. The pump impeller 26 may be received within the pump reservoir 14 in any conventional manner. As illustrated, in the preferred embodiment, the pump impeller 26 is received within the pump reservoir 14 through the removable lid 22.

The pump 16 is provided with an outlet 30 which is placed in communication with a flexible hose 38. A conduit 28 is provided for communicating water 20 from the impeller 26 to the outlet 30. Therefore, when water 20 is received within the pump reservoir 14 and the pump 16 is energized, water 20 is withdrawn from the pump reservoir 14 via the pump impeller 26 and is subsequently ejected through the outlet 30 and into the flexible hose In order to equalize the pressure within the pump reservoir 14, a vent 24 is provided. When the cleaning device be is not in use, the vent 24 may be selectively closed in order to prevent accidental leakage of the water 20 from the pump reservoir 14.

In the preferred embodiment, the pump 16 is powered using DC current. To this extent, at least one battery 34 is received within the housing 32 exterior to the pump reservoir 14. A switch 36 is also carried by the housing 32 to control the operation of the pump 16.

Figure 2:
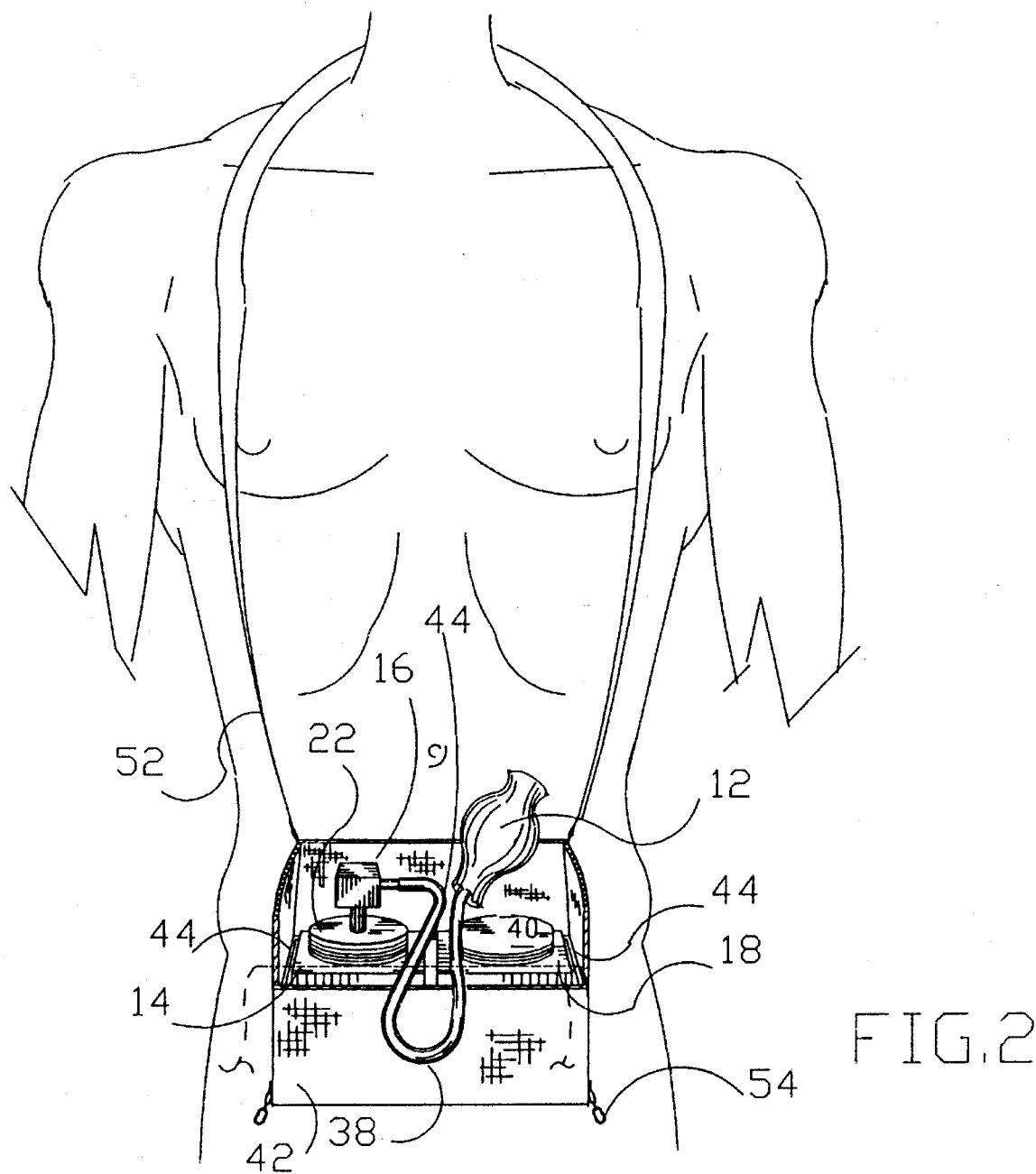
FIG. 2 is a perspective illustration of an ostomy bag cleaning device of the present invention shown in use and supported by a standing patient.

As shown in FIG. 2, the flexible hose 38 is inserted into the ostomy bag 12 to be cleaned and the pump 16 is energized. Thus, the water 20 is injected into the ostomy bag 12. The pressure of the stream of water 20 assists in scrubbing the inner wall of the ostomy bag 12. After an adequate amount of water 20 is introduced into the ostomy bag 12, the opening of the bag 12 is pinched closed and the bag 12 is then agitated. The contents are then emptied into the waste receptacle 18 or into a toilet is accessible. If a toilet is not accessible and the waste receptacle 18 is used, the waste receptacle 18 is closed using a conventional closure device such as the illustrated lid 40. Of course, other conventional closure devices may be employed as well.

The cleaning procedure described may be performed as many times as necessary in order to completely evacuate the ostomy bag 12. As required, the pump reservoir 14 is refilled. Also as required, the waste receptacle 18 is emptied to allow for further cleaning of the ostomy bag 12. To this extent, the volume within the pump reservoir 14 of the preferred embodiment is sufficient to retain enough water 20 to rinse the ostomy bag 12 several times in the manner described. Further, the volume defined within the waste receptacle 18 is sufficient to receive the water 20 evacuated from the pump reservoir 14 and the waste evacuated from the ostomy bag In order to facilitate the portability of the cleaning device 10 of the present invention, a carrying case 42 is provided for storing the pump reservoir 14 and the waste receptacle 18. In the preferred embodiment, a rigid support structure 44 is provided for receiving both the pump reservoir 14 and the waste receptacle 18 such that the position of each is maintained. The support structure 44 of the illustrated embodiment defines a box-like construction having an open top end. Thus, the pump reservoir 14 and the waste receptacle 18 are simply set into the support structure 44. In order to better maintain the position of the pump reservoir 14 and waste receptacle 18 within the support structure 44, a fastening member 46 such as a hook-and-loop fastener may be used. As illustrated, a length of such a fastener 46 is secured between each of the pump reservoir 14 and the waste receptacle 18, individually, and the inner wall of the support structure 44. Of course, other arrangements of and types of fasteners may be used as well.

The support structure 44 is received within a carrying case 42 having an opening 50 proximate the top thereof. A fastener 48 such as a hook-and-loop type fastener may be provided for maintaining the position of the support structure 44 within the carrying case 42. In the preferred embodiment, the carrying case 42 defines a substantially rectangular configuration dimensioned to closely receive the support structure 44, the pump reservoir 14, the waste receptacle 18, and any other associated components. As illustrated, one edge of the top panel defined by the carrying case 42 is secured to, or integral with, a respective side panel, with the remaining three edges defined by the top panel being unsecured. Thus, the top panel may be folded over to provide easy access to the pump reservoir 14 and waste receptacle 18, both for use and for removal. When not in use, the top panel is securable proximate the three free edges to the respective side panels of the carrying case 42.

A strap member 52 is provided for carrying the carrying case 42. Further, the strap member 52 is used to support the cleaning device 10 while the cleaning device 10 is being used to clean an ostomy bag 12. As illustrated in FIG. 2, the strap member 52 allows one to stand while performing the cleaning procedure. By providing the ability to stand while cleaning the ostomy bag 12, the time required to perform such cleaning can be reduced, as it is usually recommended that one move about in order to inhibit loosening of waste within the intestinal tract of the patient. This also allows one to cleanse an ostomy bag 12 without sitting on an unsanitary toilet found in many public rest rooms. The strap member 52 is adjustable in order to properly position the cleaning device be for each individual patient and for each individual ostomy bag placement on the patient.

During the cleaning procedure used as described above, it is often necessary for the patient to loosen their garments. Because their hands are being used to operate the cleaning device be, it can be difficult to hold their garments up. In some facilities, it is particularly undesirable to allow clothing to contact the floor. Therefor, the carrying case 42 of the present invention is provided with an engaging device 54 such as a pair of hooks to each of which may be secured a belt loop carried by the pants. Alternatively, only one hook may be provided. Further, although not shown, for pants which are not provided with belt loops, or for other types of garments, other types of fasteners may be used such as clamps. Still further, the person's clothing may be modified to include snaps or one portion of a hook-and-loop type fastener to fasten to the cooperating portion thereof carried on the carrying case.

From the foregoing description, it will be recognized by those skilled in the art that an ostomy bag cleaning device offering advantages over the prior art has been provided. Specifically, the ostomy bag cleaning device provides a means for storing water to be used in the cleaning procedure of an ostomy bag. Further, the ostomy bag of the present invention provides a means for pumping the water into the ostomy bag and for storing the waste material after the cleaning procedure has been performed. Still further, the present invention is portable such that the ostomy bag may be sanitarily cleaned even in unsanitary facilities.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. A device for cleaning a body waste bag, said device comprising:

a reservoir for retaining water;

a pump for pumping said water into said body waste bag; and a waste receptacle for receiving and storing wasted water and solid waste from said body waste bag and said water pumped from said reservoir.

2. The device of claim 1 wherein said reservoir is provided with a removable closure device for selectively opening and closing said reservoir.

3. The device of claim 1 wherein said pump includes an impeller positioned in said reservoir, an outlet positioned exterior to said reservoir, and a conduit for communicating said water from said impeller to said outlet, said device further comprising a hose for directing flow of said water into said body waste bag.

4. The device of claim 1 wherein said pump is provided with a direct current source received within a pump housing and a power switch carried by said housing for controlling operation of said direct current source.

5. The device of claim 1 wherein at least said reservoir, said pump, and said waste receptacle are received within a carrying case.

6. The device of claim 5 wherein at least said reservoir and said waste receptacle are received within a support structure for maintaining a relative position of each, said support structure defining a rigid construction and being received within said carrying case.

7. The device of claim 5 wherein a strap member is secured at opposing ends to said carrying case.

8. The device of claim 7 wherein said carrying case is provided with an engagement device for engaging a garment worn by a user of said device.

9. A device for cleaning a body waste bag, said device comprising:

a reservoir for retaining water, said reservoir being provided with a removable closure device for selectively opening and closing said reservoir;

a pump for pumping said water into said body waste bag, said pump including an impeller positioned in said reservoir, an outlet positioned exterior to said reservoir, and a conduit for communicating said water from said impeller to said outlet, said device further comprising a hose for directing flow of said water into said body waste bag; and a waste receptacle for receiving and storing wasted water and solid waste from said body waste bag and said water pumped from said reservoir.

10. The device of claim 9 wherein said pump is provided with a direct current source received within a pump housing and a power switch carried by said housing for controlling operation of said direct current source.

11. The device of claim 9 wherein at least said reservoir, said pump, and said waste receptacle are received within a carrying case.

12. The device of claim 11 wherein at least said reservoir and said waste receptacle are received within a support structure for maintaining a relative position of each, said support structure defining a rigid construction and being received within said carrying case.

13. The device of claim 11 wherein a strap member is secured at opposing ends to said carrying case.

14. The device of claim 13 wherein said carrying case is provided with an engagement device for engaging a garment worn by a user of said device.

15. A device for cleaning a body waste bag, said device comprising:

a reservoir for retaining water, said reservoir being provided with a removable closure device for selectively opening and closing said reservoir;

a pump for pumping said water into said body waste bag, said pump including an impeller positioned in said reservoir, an outlet positioned exterior to said reservoir, and a conduit for communicating said water from said impeller to said outlet, said device further comprising a hose for directing flow of said water into said body waste bag, said pump being provided with a direct current source received within a pump housing and a power switch carried by said housing for controlling operation of said direct current source;

a waste receptacle for receiving and storing wasted water and solid waste from said body waste bag and said water pumped from said reservoir; and a carrying case for receiving at least said reservoir, said pump, and said waste receptacle.

16. The device of claim 15 wherein at least said reservoir and said waste receptacle are received within a support structure for maintaining a relative position of each, said support structure defining a rigid construction and being received within said carrying case.

17. The device of claim 16 wherein a first fastening member is provided for removably securing said reservoir to said support structure and a second fastening member is provided for removably securing said waste receptacle to said support structure.

18. The device of claim 16 wherein a fastening member is provided for removably securing said support structure to said carrying case.

19. The device of claim 15 wherein a strap member is secured at opposing ends to said carrying case.

20. The device of claim 19 wherein said carrying case is provided with an engagement device for engaging a garment worn by a user of said device.

* * * * *